United States Patent
Berrevoets et al.

(10) Patent No.: US 6,517,543 B1
(45) Date of Patent: Feb. 11, 2003

(54) BONE CONNECTOR SYSTEM WITH ANTI-ROTATIONAL FEATURE

(75) Inventors: Greg A. Berrevoets, Skandia, MI (US); Thomas S. Kilpela, Marquette, MI (US); Francis J. Korhonen, Negaunee, MI (US)

(73) Assignee: Pioneer Laboratories, Inc., Marquette, MI (US)

( * ) Notice: Subject to any disclaimer, the term of this patent is extended or adjusted under 35 U.S.C. 154(b) by 0 days.

(21) Appl. No.: 09/794,516

(22) Filed: Feb. 27, 2001

Related U.S. Application Data

(63) Continuation-in-part of application No. 09/602,771, filed on Jun. 23, 2000, which is a continuation-in-part of application No. 09/499,881, filed on Feb. 8, 2000, now Pat. No. 6,413,260, which is a continuation-in-part of application No. 09/375,330, filed on Aug. 17, 1999, now abandoned.

(51) Int. Cl.[7] ............................................. A61B 17/84
(52) U.S. Cl. ...................... 606/73; 411/324; 411/419; 411/508; 606/72; 433/172
(58) Field of Search .............................. 606/53, 60, 65, 606/66, 72, 73; 433/172–174; 411/324, 419, 420, 421, 508, 509

(56) References Cited

U.S. PATENT DOCUMENTS

| | | | |
|---|---|---|---|
| 184,718 A | 11/1876 | Lewis | 403/184 |
| 1,897,196 A | 2/1933 | Hunt | 411/389 |
| 3,103,926 A | 9/1963 | Cochran et al. | 606/73 |
| 3,115,804 A | * 12/1963 | Johnson | 411/324 |
| 5,417,692 A | 5/1995 | Goble et al. | 606/73 |
| 5,564,921 A | * 10/1996 | Marlin | 433/172 |
| 5,782,918 A | * 7/1998 | Klardie et al. | 623/16 |
| 6,394,806 B1 | * 5/2002 | Kumar | 433/173 |

* cited by examiner

Primary Examiner—Nicholas D. Lucchesi
Assistant Examiner—Michael B. Priddy
(74) Attorney, Agent, or Firm—Fitch, Even, Tabin & Flannery

(57) ABSTRACT

A bone connector system includes first and second connector members, at least one and preferably both, of which carries an external bone screw thread to permit securance within a bone. One of the connector members defines a boss having an outer end with at least one slot therein to form flexible fingers, the boss having flanges which may be formed by an external screw thread adjacent to the outer end, and an external hexagonal engagement surface spaced from the outer end. The other of the connector members defines a bore having grooves which may formed by an internal screw thread proportioned to engage the flanges on the boss, and a hexagonal engagement portion proportioned to mateably receive and engage the hexagonal engagement surface when the connectors are brought together. Each of the flanges and grooves may have first and second flanks respectively disposed at relatively small and relatively large acute angles to the longitudinal axis of the system. Either or both of the connector members may define guidewire lumens.

16 Claims, 3 Drawing Sheets

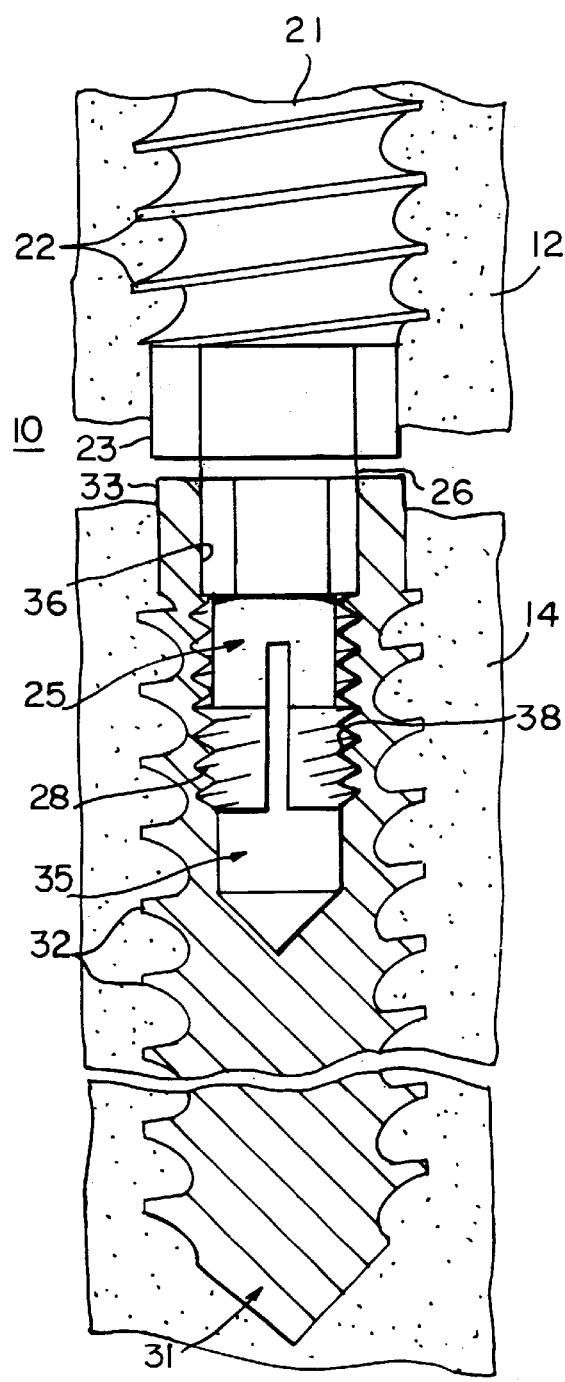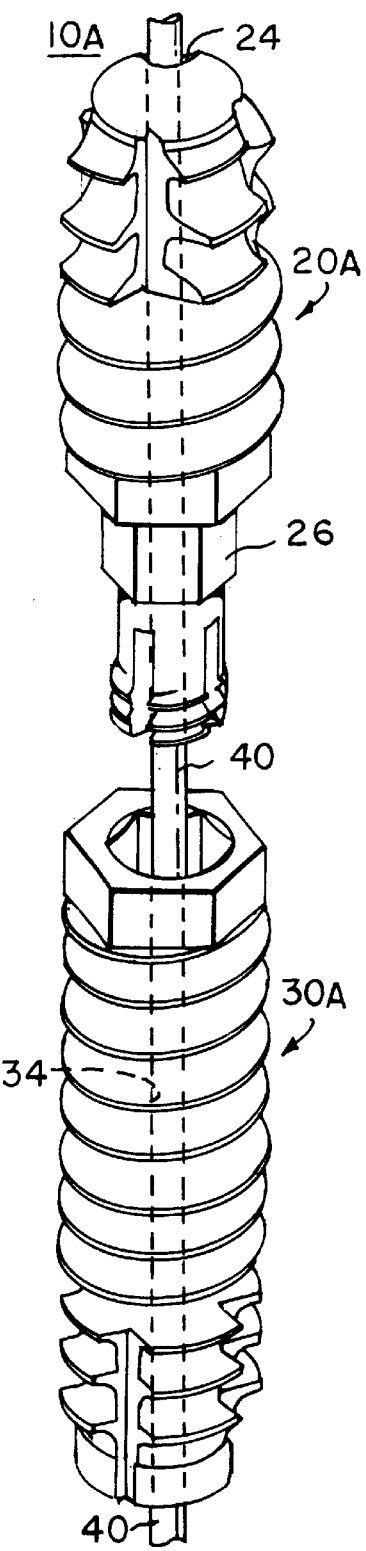
FIG. 3
FIG. 4

BONE CONNECTOR SYSTEM WITH ANTI-ROTATIONAL FEATURE

CROSS REFERENCE TO RELATED APPLICATIONS

This application is a continuation-in-part of copending U.S. application Ser. No. 09/602,771, filed Jun. 23, 2000, entitled "Bone Connector System with Anti-Rotational Feature," which is in turn a continuation-in-part of copending U.S. application Ser. No. 09/499,881, filed Feb. 8, 2000, now U.S. Pat. No. 6,413,260 entitled "Bone Connector System," which is in turn a continuation-in-part of U.S. application Ser. No. 09/375,330, filed Aug. 17, 1999, entitled "Bone Connector System," now abandoned, the disclosures of which are incorporated herein by reference.

BACKGROUND

This application relates to bone fixation and fusion systems, for example for the fusing together of toe bones or the like, by firmly locking them in abutting relation to permit good healing. This is accomplished through the use of male and female connectors, each of which, when bone fusion or fixation is the desired result, has external bone threads so that each of the connectors may be driven into a separate piece of bone or opposing ends of the same bone, as at a fracture.

The male connector is a solid body having a slotted boss with external threads adjacent to a distal end. The female connector defines an internally threaded bore in which the boss of the male connector may be threadedly engaged in a somewhat resilient, spring-like manner resulting from the cross cut slots, for retention of the two connectors together.

This threaded interconnection permits the connectors to be engaged in a well-fitting, solid connection which nevertheless is highly adjustable in its length by adjusting the depth to which one connector is inserted into the other. However, the threaded interconnection may also permit one connector to rotate with respect to the other after installation, which may be undesirable or harmful. Also, the shape of the threads of the threaded interconnection, together with the flexibility of the slotted boss, may permit a camming action which could result in the connectors being axially pulled apart if sufficient force is applied.

SUMMARY

By this invention, a bone connector system is provided which comprises first and second connector members. At least one of the connector members carries an external bone screw thread to permit securance within a bone. In the circumstance where two bones or two parts of a bone are being connected together for fusing or the like, both of the connectors may carry external bone screw threads, to permit their separate securance within separate bone parts. Otherwise, one of the connector members may connect to an artificial tooth or another attachment to a bone.

One of the connector members defines a projection or boss having a distal or outer end. One or more longitudinal slots extend through the boss adjacent to its outer end. The boss also carries a plurality of loops or convolutions of an external screw thread adjacent to the outer end. The other of the connector members defines a bore for receiving the boss, and having a plurality of loops or convolutions of an internal screw thread which is proportioned to engage the external thread of the boss when the connectors are brought together. The internal screw thread and the external screw thread may fit together with a multiple-loop, close, tight fit without any mispositioning. The screw threads have differently-sloped flanks, one inclined at a small acute angle and one at a large acute angle to the longitudinal axis of the connector, so that it is much more difficult to axially pull the connectors apart than it is to push them together.

The outer surface of the boss has a portion of non-circular peripheral shape disposed for mating engagement in a portion of the bore having a similar non-circular peripheral shape when the boss is disposed in the bone, to prevent relative rotation of the connector members.

If desired, one or both connector members may define a central lumen, to permit a guidewire to extend through either or both connector members to facilitate placement thereof at a desired position in a bone.

BRIEF DESCRIPTION OF THE DRAWINGS

FIG. 3 is an enlarged, fragmentary view in partial longitudinal section of the bone connector system of FIG. 1, shown in a position of implantation within and connecting two bones;

FIG. 4 is a perspective view similar to FIG. 1 of a modified bone connector system.

DETAILED DESCRIPTION

Figure 1:
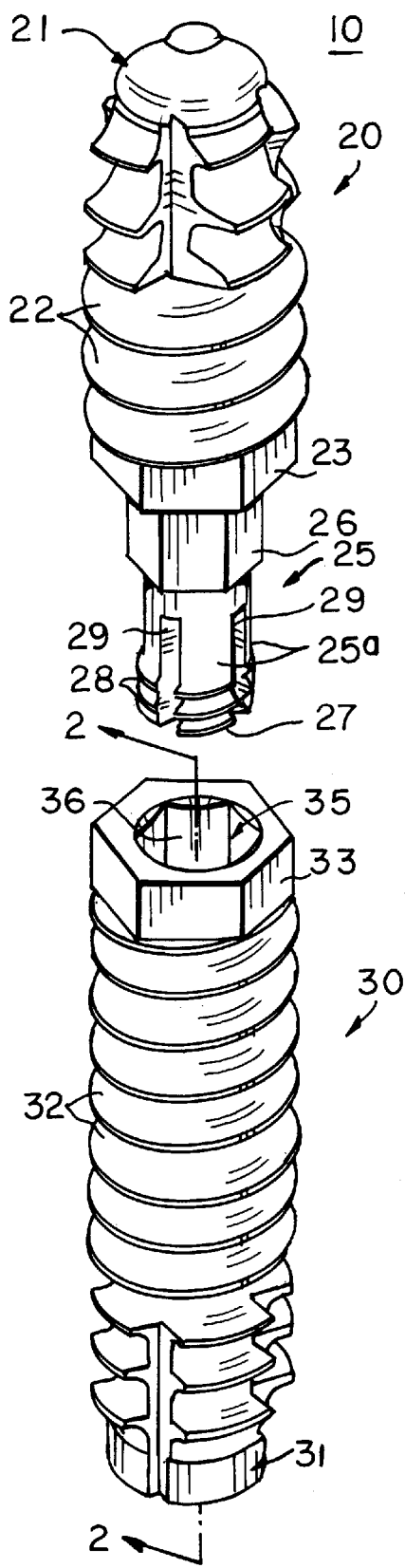
FIG. 1 is a perspective view showing the two separate connector members of the bone connector system of the invention.
Figure 2:
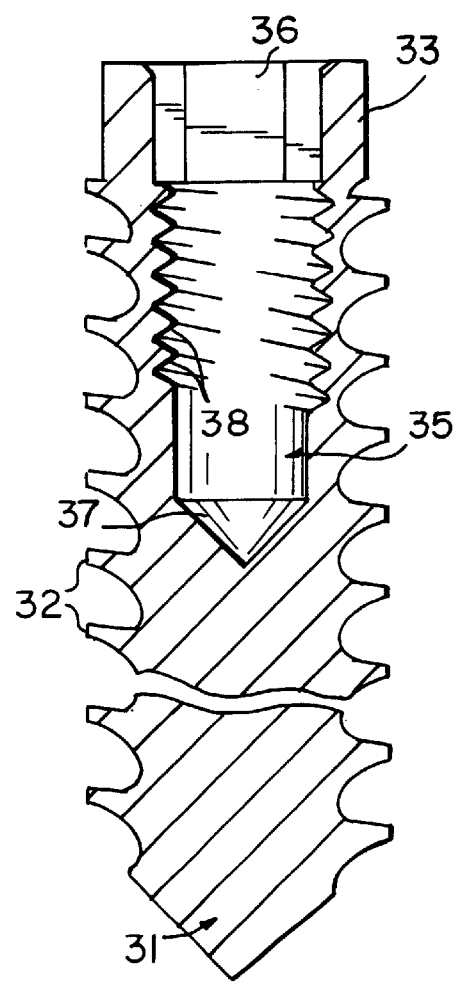
FIG. 2 is an enlarged sectional view, taken generally along line 2—2 of FIG. 1, of one of the connector members.

Referring to FIGS. 1–3, bone connector system 10 is shown in FIG. 3 to be implanted between a pair of bones or parts of a bone 12, 14, for example, two bone parts in a toe which need fusion, and are so fused by the installation of the bone connector system 10.

The bone connector system 10 includes two bone connector members 20 and 30, each of which may be made of a desirable surgically implantable metal. The connector member 20 has an elongated body 21 provided with an external bone screw thread 22 so that the connector member 20 can be fixed in an associated bone or bone part. The connector member 20 also has an external polygonal drive surface 23, which may be hexagonal in shape, to receive an associated wrenching tool or the like to facilitate implanting the connector member 20 in the associated bone or bone part, in a known manner.

The connector member 20 also defines a projecting boss 25 which has an external peripheral engagement surface 26 which is non-circular in shape. The surface 26 may have a polygonal shape, such as hexagonal. The boss 25 has an outer or distal end 27 and is provided with an external thread 28 adjacent to the distal end 27, the loops or convolutions of the thread 28 forming laterally outwardly projecting flanges. Formed in the boss 25 adjacent the distal end 27 are one or more slots 29 (two shown). The slots 29 may be equiangularly spaced around the periphery of the boss 25, with the slots communicating with one another internally of the boss 25, so that the slots 29 cooperate to divide the boss 25 into a plurality of fingers 25a.

The connector member 30 has an elongated body 31 and is provided with an external bone screw thread 32 so that it can be fixed in an associated bone or bone part. The connector member 30 has an external peripheral drive surface 33, which may be polygonal in shape, such as hexagonal, to receive an associated wrenching tool and the like to facilitate implanting the connector member 30 in an associated bone or bone part. Formed in the connector member 30 is a bore 35 which could extend entirely or part-way through the connector member 30. The bore 35 is provided adjacent to an outer end with a peripheral engagement portion 36 which is non-circular in shape, being shaped and dimensioned for mating engagement with the engagement surface 26 of the connector member 20. More specifically, the engagement portion 36 may be polygonal, such as hexagonal. The bore 35 is provided, inboard of the engagement portion 36, with an internal screw thread 38, having plural loops or convolutions which define grooves which form another engagement portion. The screw thread 38 is designed for threaded engagement with the screw thread 28 of the connector member 20.

In use, if two bones or two parts of a bone 12, 14 are to be fused togther, the connector members 20 and 30 are, respectively, screwed into the bones or bone parts in a known manner to fixed positions illustrated in FIG. 3. Then, the connector members 20 and 30 are secured together by inserting the boss 25 into the bore 35. This insertion may be accomplished without relative rotation of the parts, because the fingers 25a of the boss 25 have radial flexibility sufficient to permit them to be deflected inwardly so that the loops or convolutions of the external screw thread 28 on the boss 25 can be snapped past the loops or convolutions of the internal screw thread 38 in the bore 35 in a camming action. The boss 25 is in inserted in the bore 35 until the hexagonal engagement surface 26 enters the hexagonal engagement portion 36 of the bore 35. In this regard, it will be appreciated that, when the connector members 20 and 30 are respectively inserted in the bones 12 and 14, they will be rotated to positions wherein the engagement surface 26 and the engagement portion 36 align with each other. It will also be appreciated that the boss 25 may be inserted into the bore 35 to a variety of different depths, limited by the axial extent of the hexagonal engagement portion 36 of the bore 35, so that the overall length of the bone connector system 10 may be finely adjustable.

Once the engagement surface 26 is mateably engaged with the engagement portion 36, the connector members 20 and 30 are non-rotatable relative to each other.

While the invention has been described with respect to fusing of toe bones or bone parts, it will be appreciated that the bones 12 and 14 may be other types of bones, such as finger bones, adjacent vertebrae or any other adjacent bones which need to be fused together. If only one of the connector members 20 and 30 is mounted in a bone, it will be appreciated that, in joining the other connector member to it, the other connector member may initially be rotated to screw the parts together until the engagement surface 26 is about to enter the engagement portion 36, whereupon continued joinder is accomplished by an axial movement.

While the flanges on the boss 25 and the grooves in the bore 35 are respectively formed by helical threads 28 and 38, they could be discrete, annular flanges and grooves, but threads are less expensive to form.

Referring to FIG. 4, an alternative design of the bone connector system designated 10A is illustrated, including connector members 20A and 30A, which are respectively substantially the same as the connector members 20 and 30, described above, except that the connector members 20A and 30A respectively define central lumens 24 and 34 extending longitudinally therethrough. This permits the connector members 20A and 30A to be threaded onto a guidewire 40 to facilitate advancement and placement of the respective connector members 20A and 30A into their desired positions.

Figure 5:
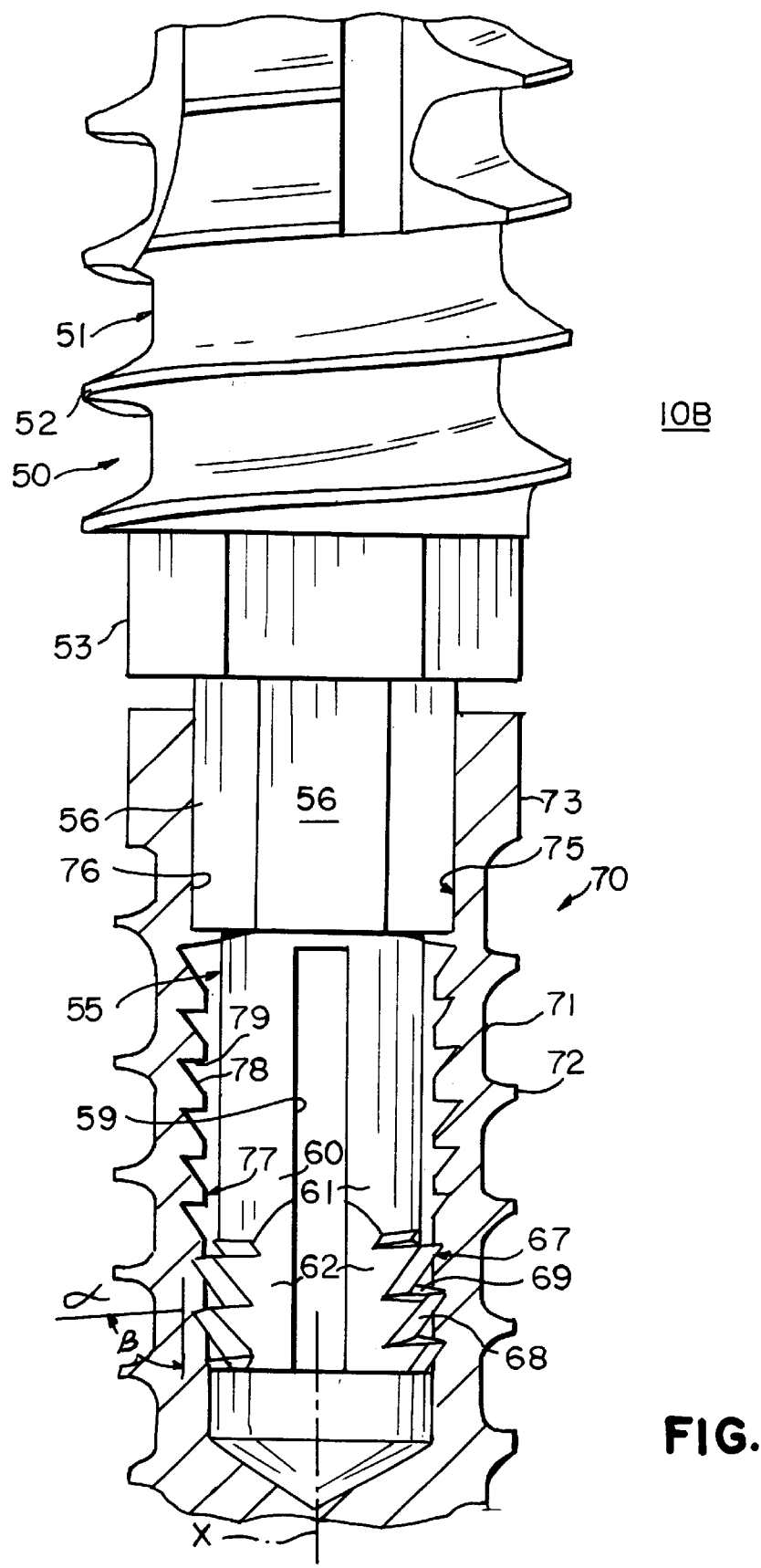
FIG. 5 is a fragmentary view in partial section similar to FIG. 3, illustrating another embodiment of the bone connector system.

Referring to FIG. 5, there is illustrated a bone connector system 10B, which is similar in construction and operation to the bone connector system 10 of FIG. 3, except for the differences described below. The system 10B includes a connector member 50, similar to the connector member 20, having an elongated body 51 provided with an external bone screw thread 52 and an external polygonal drive surface 53, which may be hexagonal in shape. The connector member 50 also defines a projecting boss 55 which has an external peripheral engagement surface 56 which is non-circular in shape. The surface 56 may have a polygonal shape, such as hexagonal. The boss 55 has an outer or distal end which has formed therein a diametral slot 59 which divides the end of the boss 55 into fingers 60 and 61, each of which has side faces 62 which intersect the slot 59 at an angle thereto. The boss 55 is provided with an external thread 67 adjacent to the distal end, the loops or convolutions of the thread 67 forming laterally outwardly projecting flanges, each of which has a first or lower face or flank 68 inclined at a relatively small acute angle a to the longitudinal axis X of the connector member 50, and an upper or second face or flank 69 disposed at a relatively large angle β to the axis X.

The system 10B also includes a connector member 70 having an elongated body 71 provided with an external bone screw thread 72. The connector member 70 has an external peripheral drive surface 73, which may be polygonal in shape, such as hexagonal. Formed in the connector member 70 is a bore 75 which could extend entirely or part-way through the connector member 70. The bore 75 is provided adjacent to an outer end thereof with a peripheral engagement portion 76 which is non-circular in shape, being shaped and dimensioned for mating engagement with the engagement surface 56 of the connector member 50. More specifically, the engagement portion 76 may be polygonal, such as hexagonal. The bore 75 is provided, inboard of the engagement portion 76, with an internal screw thread 77, having plural loops or convolutions which form another engagement portion. The screw thread 77 is designed for threaded engagement with the screw thread 67 of the connector member 50, each loop or convolution of the screw thread 77 having a lower or first flank or face 78 disposed at the angle a to the longitudinal axis of the connector member 70 and a second or upper flank or face 79 disposed at the angle β to the longitudinal axis of the connector member 70.

In use, the connector members 50 and 70 are secured together by inserting the boss 55 into the bore 75 in the same manner as was described above in connection with the system 10 of FIG. 3. During this insertion, the flexibility of the fingers 60 and 61 permits the lower flanks 68 of the boss 55 to be cammed along and past the lower flanks 78 of the connector member 70. Once the connector member 50 is connected to the connector member 70, as illustrated in FIG. 5, the upper flanks 69 of the boss 55 will be disposed in engagement with upper flanks 79 of the connector member 70. In this regard, it will be appreciated that, when the connector members 50 and 70 are joined together as in FIG. 5, they are coaxial having the common longitudinal axis X. The angle β of these flanks is relatively large, preferably approximately 90°, so separation of the connector members 50 and 70 by pulling the boss 55 axially back out of the bore 75 will be extremely difficult, if not impossible, without damage to or destruction of the parts. The angle α may be less than 45°, while the angle β may be greater than 60° and, in a preferred embodiment, the angle α is 35° and the angle β is 90°. While the angle β may slightly exceed 90°, if it is substantially greater than 90° it will create manufacturing problems and could provide a camming action which might aid attempted separation of the parts. It can be seen that, in the illustrated embodiment, the angles α and β, are such that the thread flanks define a generally Z-shape in transverse cross section.

The matter set forth in the foregoing description and accompanying drawings is offered by way of illustration only and not as a limitation. While particular embodiments have been shown and described, it will be obvious to those skilled in the art that changes and modifications may be made without departing from the broader aspects of applicants' contribution. The actual scope of the protection sought is intended to be defined in the following claims when viewed in their proper perspective based on the prior art.

We claim:

1. A bone connector system comprising:
   first and second connector members,
   at least the first connector member having structure to permit implanting into a bone,
   the second connector member having a bore therein,
   the bore having an engagement portion with internal peripheral grooves,
   the first connector member having a boss dimensioned to be received in the bore for cooperation therewith to define a common longitudinal axis,
   the boss having a distal end with a slot extending transversely through the boss at the distal end,
   the boss having external peripheral flanges adjacent to the distal end disposed for engagement in the grooves when the boss is received in the bore,
   each flange and each groove having a first flank disposed at a first relatively small acute angle to the longitudinal axis and a second flank disposed at a second relatively large angle to the longitudinal axis and a second flank disposed at a relatively large angle to the longitudinal axis, and
   an external drive surface of the first connector member generally disposed axially between said structure to permit implanting into a bone and the boss so that with the first connector member implanted into a bone from an exposed surface thereof with the drive surface adjacent thereto, the boss including the external flanges will project outward from the exposed bone surface for being inserted into the bore of the second connector member.

2. The system of claim 1, wherein the boss includes fingers separated by the slot, each finger having side faces intersecting the slot.

3. The system of claim 1, wherein the first angle is less than 45° and the second angle is greater than 60°.

4. The system of claim 3, wherein the first angle is substantially 35° and the second angle is substantially 90°.

5. The system of claim 1, wherein the grooves are formed by an internal helical thread and the flanges are formed by an external helical thread.

6. The system of claim 1, wherein the grooves are greater in number than the flanges.

7. The system of claim 1, wherein each of the connector members has a lumen extending therethrough.

8. A bone connector system comprising:
   first and second connector members,
   at least one of the connector members having structure to permit attachment to a bone,
   one of the connector members having a bore therein,
   the bore having an engagement portion with internal peripheral grooves,
   the other of the connector members having a boss dimensioned to be received in the bore for cooperation therewith to define a common longitudinal axis,
   the boss having a distal end with a slot extending transversely through the boss at the distal end,
   the boss having external peripheral flanges adjacent to the distal end disposed for engagement in the grooves when the boss is received in the bore,
   each flange and each groove having a first flank disposed at a relatively small acute angle to the longitudinal axis and a second flank disposed at a relatively large angle to the longitudinal axis and a second flank disposed at a relatively large angle to the longitudinal axis, wherein each of the connector members has external bone screw threads.

9. A bone connector system comprising:
   first and second connector members,
   at least one of the connector members having a structure to permit attachment to a bone,
   one of the connector members having a bore therein having an outer end,
   the bore having a first engagement portion of non-circular peripheral shape adjacent to the outer end,
   the bore having a second engagement portion with internal peripheral grooves disposed inboard of the first engagement portion,
   the other of the connector members having a boss dimensioned to be received in the bore for cooperation therewith to define a common longitudinal axis,
   the boss having a distal end with a slot extending transversely through the boss at the distal end,
   the boss having an outer engagement surface of non-circular peripheral shape disposed for mating engagement with the first engagement portion when the boss is received in the bore, the boss having external peripheral flanges adjacent to the distal end disposed for engagement in the grooves when the boss is received in the bore, each flange and each groove having a first flank disposed at a first relatively small acute angle to the longitudinal axis and a second flank disposed at a second relatively large angle to the longitudinal axis.

10. The system of claim 9, wherein each of the connector members has external bone screw threads.

11. The system of claim 9, wherein each of the first engagement portion and the engagement surface is polygonal in shape.

12. The system of claim 11, wherein each of the first engagement portion and the engagement surface is hexagonal in shape.

13. The system of claim 9, wherein at least one of the connector members has a lumen extending therethrough.

14. The system of claim 9, wherein the grooves are formed by an internal helical thread and the flanges are formed by an external helical thread.

15. The system of claim 9, wherein the first angle is substantially less than 45° and the second angle is substantially greater than 60°.

16. A bone connector system comprising:

first and second connector members, at least the second connector member having structure to permit implanting into a bone, the second connector member having a bore therein having an outer end including an opening to the bore, the bore having an engagement portion with internal peripheral grooves, the first connector member having a boss dimensional to be received in the bore for cooperation therewith to define a common longitudinal axis, the boss having a distal end with a slot extending transversely through the boss at the distal end, the boss having external peripheral flanges adjacent to the distal end disposed for engagement in the grooves when the boss is received in the bore, each flange and each groove having a first flank disposed at a relatively small acute angle to the longitudinal axis and a second flank disposed at a relatively large angle to the longitudinal axis and a second flank disposed at a relatively large angle to the longitudinal axis, and an external drive surface of the second connector member extending about the opening at the bore outer end to allow the second connector member to be implanted into the bone from an exposed surface thereof with the drive surface adjacent the exposed bone surface for receipt of the first connector member boss through the opening adjacent the exposed bone surface and into the bore of the implanted second connector member.

* * * * *